United States Patent [19]

della Valle et al.

[11] Patent Number: 5,122,598

[45] Date of Patent: Jun. 16, 1992

[54] POLYSACCHARIDE ESTERS

[75] Inventors: Francesco della Valle, Padua; Aurelio Romeo, Rome, both of Italy

[73] Assignee: Fidia S.p.A., Abano Terme, Italy

[21] Appl. No.: 350,920

[22] Filed: May 12, 1989

[30] Foreign Application Priority Data

May 13, 1988 [IT] Italy .................. 47963 A/88

[51] Int. Cl.$^5$ .............. C08B 37/08; A61K 9/08; A61K 9/14; A61K 9/48

[52] U.S. Cl. .............. 536/20; 424/420; 424/427; 424/436; 424/443; 424/451; 424/452; 424/456; 424/461; 424/479; 424/488; 424/489; 424/DIG. 15; 514/912; 514/953; 514/960; 514/962; 514/965; 514/969

[58] Field of Search ............ 536/20; 514/777, 912, 514/953, 960, 962, 965, 969; 424/493, 461, 479, 488, 422, 427, 436, 443, 451, 452, 456, 464, DIG. 15, 489

[56] References Cited

U.S. PATENT DOCUMENTS

| | | | |
|---|---|---|---|
| 2,912,430 | 11/1959 | Kosche | 536/66 |
| 3,092,619 | 6/1963 | Koehler et al. | 536/66 |
| 4,304,905 | 12/1981 | Koshugi | 536/20 |

FOREIGN PATENT DOCUMENTS 104467 4/1984 European Pat. Off.
251905 1/1988 European Pat. Off.

OTHER PUBLICATIONS

Roberts et al., Carbohydrate Research, 168, pp. 103-109 (1987).

Primary Examiner—Thurman K. Page
Assistant Examiner—Carlos Azpuru
Attorney, Agent, or Firm—Birch, Stewart, Kolasch & Birch

[57] ABSTRACT

New polysaccharide esters are disclosed, and more precisely esters of acidic polysaccharides chosen from the group formed by carboxymethylcellulose, carboxymethyl starch and carboxymethylchitin. These new esters and some esters of the type already known are useful as medicaments, for the manufacture of pharmaceutical and cosmetic preparations, in the field of biodegradable plastic materials and, therefore, for the manufacture of medical, surgical and sanitary articles, as well as numerous other industrial sectors in the place of acidic polysaccharides now in common use.

50 Claims, No Drawings

POLYSACCHARIDE ESTERS

SUMMARY

The present invention concerns new polysaccharide esters and more precisely esters of acidic polysaccharides chosen from the group formed by carboxymethylcellulose, carboxymethylchitin and carboxymethyl starch. The invention also includes the use of these new esters and some esters of the type already known for new uses and more precisely as medicaments, for the manufacture of pharmaceutical and cosmetic preparations, in the sector of biodegradable plastic materials and, therefore, for the manufacture of medical, surgical and sanitary articles, in galenicals and in numerous industrial sectors in the place of acidic polysaccharides now in use, such as alginic acid, especially in the food industry. The invention also includes the articles resulting from these various uses.

DETAILED DESCRIPTION OF THE INVENTION

The esters according to the present invention include total esters and partial esters. In the partial esters the nonesterified carboxy groups may be salified with metals or organic bases.

The carboxymethyl derivatives of the abovesaid natural polysaccharides, can be obtained by methods described in literature, essentially by treatment of the same with halo-acetic acids, such as chloroacetic acids, or their salts. The polysaccharides used in these preparation method and which are therefore the basis of the new esters of the present invention, may have a wide range of molecular weights, such as those of the various types of starch of cellulose and chitin present in natural materials.

There are already reports in literature of "carboxymethlcellulose esters" prepared by alkylation of the carboxy hydroxyl with diazomethane or with the alcohol corresponding to the alkyl groups to be introduced in the presence of a strong acid. In this way partial esters are obtained which do not however seem to be pure esters. Thus, in the German patent No. 957,938 carboxymethylcellulose is esterified at about 0° C. with alcohol (methyl, propyl, butyl and octyl) and gasseous hydrochloric acid. In the case of methyl alcohol the reaction is effected over a period of 48 hours, long enough for the glucoside structures present in the polysaccaride to be destroyed and no longer remain intact (see: Methanolysis of Polysaccharides; Carbohydrate Research 168 (1987) 103–109).

The same can be said of the products obtained according to the procedure described in U.S. Pat. No. 2,912,430. The preparation procedure for the methyl ester of carboxymethylcellulose described in LATV; PSR Zinat. Akad. Vestis. Kim. r. 1982/5 624–7 regards carboxymethylcellulose with diazomethane; this reagent is too drastic to leave intact the alcoholic hydroxyl groups of the polysaccharide; this ester is to be considered an ether ester of carboxymethylcellulose.

Other preparations have been made of esters of bivalent alcohols of carboxymethylcellulose obtained by the action on the same of ethylene or propylene oxides (see Belgian patent No. 656,949, Japanese patents Nos. 70.36.143 and 74.18.981). Unknown however are esters of superior bivalent alcohols, that is, those with 4 or more carbon atoms.

Some esters of monovalent alcohols of carboxymethyl starch have been described too: thus, in the publication "Staerke" 1977, 29(4), 126–8, two types of carboxymethyl starch, one with low viscosity and one with high viscosity were benzylated with benzyl chloride in alkaline conditions at 60° and benzyl esters were obtained, in which however the Polysaccharide was found to be partially decarboxymethylated.

The methyl ester of carboxymethyl starch was prepared by reacting starch with methylmonochloroacetate in methanol or benzene solution. The product proved to be esterifed to an extent of about 50% (Zesz. Nauk. Politech. Lodz, Che. Spozyw. 1977, 29, 5–17). No carboxymethylchitin esters have been described in literature.

The esters of the carboxymethyl derivatives of the abovesaid polysaccharides obtained according to the abovesaid methods are always partial esters. Up till now it has not been possible to prepare total esters by such methods. Thanks to a new procedure of the present invention, it is now possible to have access to the total esters of the abovesaid carboxymethyl derivatives too. The new method consists in treating quaternary ammonium salts of the abovesaid acidic polysaccharides with an alkylating or etherifying agent in an aprotic solvent, especially in dimethylsulfoxide. By this method it is possible to prepare not only the total esters of the abovesaid monovalent or bivalent alcohols, but also the whole range of esters deriving too from alcohols of other series, such as alicyclic or heterocyclic esters, even those with quite complicated structures, which could not be obtainable by the prior methods used in the art.

As a result, one of the main objects of the present invention is to provide new total or partial esters of the polysaccharides chosen from the group formed by carboxymethylcellulose, carboxymethyl starch and carboxymethylchitin with alcohols of the aliphatic, aralipahtic, cycloaliphatic or heterocyclic series and by the salts of such partial esters with inorganic or organic bases, with the exception of the partial esters of carboxymethylcellulose with ethylene- and propyleneglycol and the methyl and benzyl ester of carboxymethyl starch.

A second object of the invention is represented by a new procedure for the preparation of esters, of carboxymethylcellulose, carboxymethyl starch and carboxymethylchitin, characterized by treating a quaternary ammonium salt of one of these polysaccharide derivatives with an etherifying agent in an aprotic solvent, and, if desired, salifying in the partial esters thus obtained the free carboxy groups with pharmacologically acceptable inorganic or organic bases A third object of the invention is represented by the use of esters of the abovesaid derivatives of the three carboxymethylpolysaccharides, including the known ones, in the fields of medicine, pharmaceuticals and cosmetics and in the following industrial sectors:
1. food industry
2. paper industry
3. adhesive products
4. printing
5. textile dyes
6. in the preparation of sanitary, medical and surgical products
7. in galenics for the preparation of capsules and microcapsules
8. in biology to immobilize enzymes 9. as emulsifyers for polishes, anti-foam agents, lactics and as stabilizers in the ceramic and detergent industries A fourth object of the invention is represented by industrial articles or products made with esters for the aforesaid uses and which will be described in more detail hereafter.

The esters of the present invention or their salts may themselves be medicaments, whenever the alcohols which make up the ester group are therapeutically active or when the bases salifying free carboxy groups of partial esters are therapeutically active. In such cases the polysaccharide ester acts as a vehicle for such therapeutically active substances and medicaments in the form of such esters, possibly associated with other conventional excipients for pharmaceutical preparations. These esters have properties which are qualitatively similar to those of the therapeutically active alcohol used as the esterifying agent, or similar to that of the therapeutically active base used as the salifying component or of both these categories of substances. However, the new esters of the invention have a more differentiated range of action, even with regard to the known esters, ensuring a more balanced, constant and regular pharmacological action and usually achieving a marked retard effect.

One particular case of such medicaments is represented by esters in which one part of the carboxy groups is esterified with therapeutically active alcohols and another part with pharmacologically indifferent alcohols, or whose activity is negligible. By suitably dosing the percentages of the two types of alcohol as esterifying component, it is possible to obtain esters with the same activity as the pharmacologically active alcohol and in which the abovesaid properties of increased bioavailability and stability are made full use of. Lastly, it is possible to prepare mixed-type esters in which the ester groups derive from two different therapeutically active alcohols, for example from a cortisone steroid and from an antibiotic, while other carboxy groups may be free or salified, for example, with alkaline metals, especially with sodium.

It is however also possible to prepare esters with three or more alcohol components, for example esters in which part of the carboxy groups are esterifed with a therapeutically active alcohol, another part with another therapeutically active alcohol, a third part with a therapeutically inactive alcohol and a fourth part is possibly salified with a metal or with a therapeutically active or inactive base, or it is in free form.

The vehicling of therapeutically active substances, apart from the esterification of therapeutically active alcohols, can also be achieved by the simple association of an ester of the type of the present invention (new or known) with the therapeutically active substance, that is, in a physical mixture. In this case it is preferable to use carboxymethyl esters derived from cellulose starch and chitin esters with therapeutically indifferent alcohols, and the therapeutically active substance may be for example of an acidic or neutral character. If the esters of the carboxymethyl polysaccharide derivatives are partial, the free carboxy groups may be salified with inorganic or organic bases. By using therapeutically active bases for the salification, it is possible to obtain stechiometrically neutral salts or acid salts or basic salts according to the quantity of base used for the salification and the use of these salts therefore constitutes another way of vehicling the medicaments through the esters of the present invention. Regarding the vehicling action of the new esters and also of those already known (since this property has never been described in literature) it is possible therefore to prepare new medicaments including:

1. a pharmacologically active substance or an association of two or more such substances; and
2. a total or partial ester of a carboxymethyl derivative of cellulose, starch, or chitin or one of its salts and such medicaments are a further object of the invention.

The esters to be used in these medicaments are above all those in which the esterifying alcohol is itself not pharmacologically active, for example a simple aliphatic alcohol, such as one of those named hereafter. The invention does not however exclude medicaments of this type in which the ester too is pharmacologically active, such being the case for example of one of the abovesaid esters deriving from pharmacologically active alcohols.

In such medicaments, where partial esters are used, possible salification of the remaining carboxy groups is carried out preferably with therapeutically neutral inorganic or organic bases, especially with alkaline metals, such as sodium or ammonium. Should the active substance 1) or a corresponding association of substances have basic groups, such as for example antibiotics containing amino groups, and should partial esters of acidic carboxymethyl-polysaccharide acid be used with remaining free carboxy groups, the corresponding salts are formed between these and the basic substances. The basic substance may of course be in excess, producing basic salts, or in an amount less than that needed to salify all carboxy groups, producing acid salts. The new medicaments therefore include in particular the partial esters of carboxymethyl-polysaccharide acid partially salified with pharmacologically active substances of a basic character, as described above. The nonesterified carboxy groups may themselves be salified with therapeutically active bases, even where the vehicled substance is not of a basic nature.

Carboxymethyl-polysaccharide esters are particularly useful as vehicles in ophthalmology, where a particular compatibility is to be noted between the new products and the corneal epithelium, and therefore excellent tolerability with no sensitization effects.

Furthermore, when the medicaments are administered in the form of concentrated solutions with elastic, viscous characteristics or in solid form, it is Possible to obtain homogenous, stable, perfectly transparent and adhesive films on the corneal epithelium which also guarantee prolonged bioavailability of the drug and which represent excellent retard effect preparations. Such ophthalmic medicaments are exceptionally valuable in the veterinary field, considering that there are at present no veterinary preparations containing chemotherapeutic substances for use in the eyes. Indeed, preparations for human use are normally used for animals too, and these do not always guarantee a specific range of action or they do not always allow for the particular conditions under which treatment must take place. This is the case, for example of therapy for infections keratoconjuntivitis, pink eye or IBK, an infection which mainly affects cattle, sheep and goats. Presumably these three species have specific etiologic factors and more particularly: in cattle the main microorganism involved would appear to be Moraxella bovis (even though it is not possible to exclude other agents of a viral origin, such as Rhinotracheitis virus, in sheep Micoplasma, Rickettsiae and Clamidiae, in goats Rickettsiae).

The disease manifests itself in acute form and tends to spread rapidly: in the initial stages the symptoms are characterized by blepharospasm and excessive lacrimation, followed by purulent exudate, conjunctivitis and keratitis, often associated with high temperature, reduced appetite and milk production. Particularly serious are the corneal lesions which in the final stages may even cause Perforation of the cornea itself. The clinical course of the disease varies from a few days to several weeks. A vast range of chemotherapeutic agents are used in treatment, administered both topically (often associated with steroid antiinflammatory agents), and systemically, and among these are: tetracyclines, such as oxytetracycline, penicillins, such as cloxacillin and benzylpenicillin, sulfamides, polymixin B (associated with miconazole and prednisolone), chloramphenicol and tylosin. Topical treatment of the disease, despite its apparent simplicity, is still open to debate, since the ocular preparations used to date do not, for one reason or another, allow therapeutically efficacious concentrations of antibiotic or sulfamide to be obtained in the tears. This is understandable in the case of solutions, considering the predominantly tilted position of the head in the above animals, but it is also true of the semi-solid medicaments, as the excipients normally used in the same do not adhere sufficiently to the surface of the cornea, since they do not generally have a high enough concentration of active substance and are impossible to satisfactorily distribute over the surface to be treated (presence of a distribution gradient).

These drawbacks to conventional eye drops used in ophthalmology have been described by Slatter et al. in "Austr. vet. J.," 1982, 59 (3), pp. 69-72.

With the esters of the present invention these difficulties can be overcome. The presence of carboxymethyl-polysaccharide ester as vehicle for ophthalmic drugs does indeed allow the formulation of excellent preparations free from concentration gradients of the active substance and therefore perfectly homogenous, perfectly transparent and perfectly adhesive to the corneal epithelium, free from sensitization effects and with the active substance contained in an excellent vehicle and possibly with a retard effect.

The above properties of the new medicaments can of course also be put to use in other fields besides ophthalmology: they can be applied in dermatology and in infections of the mucus, for example of the mouth.

They can also be used to obtain a systemic effect thanks to transcutaneous absorption, for example in suppositories. All these applications are feasible both in human and veterinary medicine. In human medicine the new medicaments are particularly suitable for use in pediatrics. The present invention therefore also includes in particular any one of these therapeutic applications.

For the sake of brevity, reference hereinafter to the active substance of component 1) according to the invention should be understood to encompass the presence of a single active substance and also the association or mixture of two or more active substances Component 1) defined above may first and foremost be enumerated according to its use in various fields of therapy, beginning with the distinction between human and veterinary medicine and then specifying the various sectors of application with regards to the organs or tissues to be treated, such as ophthalmology, dermatology, otorhinolaryngology, gynaecology, angiology, neurology or any other type of pathology of the internal organs which can be treated by topical applications, such as rectal applications. According to one particular aspect of the present invention, the pharmacologically active substance 1) is first and foremost a substance for ophthalmic use. On the basis of another criterion the pharmacologically active substance 1) should be distinguished with regard to its effect and may therefore, for example, be in the form of an anesthetic, analgesic, antiinflammatory drug, a vasoconstrictor, antibacterial, or antiviral. For the ophthalmic sector it can be indicated particularly and for example for its: miotic, antiinflammatory, wound healing and antimicrobial effects. Component 1) may also be, according to the invention, an association of two or more active substances, as contained in many known medicaments. For example, in ophthalmology, they may be associated with an antibiotic, an antiphlogistic and a vasoconstrictor or with several antibiotics one or more antiphlogistics, or with one or more antibiotics, a mydiatric or miotic or wound healing agent or an antiallergic etc. For example the following associations of ophthalmic drugs may be used: kanamycin+phenylephrine+dexamethasone phosphate, kanamycin+betamethasone phosphate +phenylephrine, or similar associations with other antibiotics used in ophthalmology, such as rolitetracycline, neomycin, gentamycin, tetracyline. In dermatology it is possible to have as active component 1) associations of various antibiotics, such as erythromycin, gentamycin, neomycin, gramicidin, polymyxin B, between themselves, or of the same antibiotics with antiinflammatory agents, for example corticosteroids, for example hydrocortisone+neomycin, hydrocortisone+-neomycin+polymyxin B+gramicidin, dexamethasone+neomycin, fluorometholone +neomycin, prednisolone+neomycin, triamcinolone+neomycin+-gramicidin+nystatin, or any other association used in conventional dermatological preparations. Associations of different active substances are not of course limited to this field, but in each of the abovesaid fields of medicine it is possible to use associations similar to those already in use for the pharmaceutical preparations known to the art.

In the case referred to above of the use of a basic-type substance 1), the salts which are formed with a partial carboxymethyl-polysaccharide ester may be of various types, and that is, the remaining carboxy groups may be salified, or only an aliquot part, thus obtaining acid salts—esters, or neutral salts—esters. The number of acidic groups to be kept free may be important for the preparation of medicaments with a particular pH. According to one particular aspect of the invention it is possible to prepare medicaments of this type starting from previously isolated and possibly purified salts, in an anhydrous solid state, as amorphous powders which on contact with the tissue to be treated constitute a concentrated aqueous solution of a gelatinous character, viscous in consistency and with elastic properties. These qualities are maintained even at higher dilutions and it is therefore possible to use, instead of the abovesaid anhydrous salts, more or less concentrated solutions in water or in physiological solution, possibly with the addition of other excipients or additives, such as other mineral salts to regulate the pH and the osmotic pressure It is of course also possible to use salts to make gels, inserts, creams or ointments, containing other excipients or ingredients used in traditional formulations of these pharmaceutical preparations.

According to one preferential aspect of the invention however, medicaments containing the carboxymethylpolysaccharide ester or its salts are used alone as the vehicle with therapeutically active or inactive substances (apart from possibly aqueous solvent). Also included in the invention are those mixtures obtainable for all the types of medicament described here and also mixtures of such medicaments, such as possibly also mixtures of carboxymethyl-polysaccharide esters with the corresponding free acid groups or mixtures of their salts, for example sodium salts.

Examples of pharmacologically active substances 1) to be used in ophthalmic medicaments according to the invention are: basic or nonbasic antibiotics, for example aminoglycosides, macrolides, tetracyclines and peptides, for example gentamycin, neomycin, streptomycin, dihydrostreptomycin, kanamycin, amikacin, tobramycin, spectinomycin, erythromycin, oleandomycin, carbomycin, spiramycin, oxytetracycline, rolitetracycline, bacitracin, Polymyxin B, gramicidin, colistin, chloramphenicol, lincomycin, vancomycin, novobiocin, ristocetin, clindamycin, amphotericin B, griseofulvin, nystatin and possibly their salts, such as sulfates or nitrates, or associations between themselves or with other active principles, for example those named hereafter.

Other ophthalmic drugs to be used to advantage according to the present invention are: other antiinfectious agents such as diethylcarbamazine, mebendazole, sulfamidics such as sulfacetamide, sulfadiazine, sulfisoxazole; antivirals and antitumorals such as iododeoxyuridine, adenine arabinoside, trifluorothymidine, acyclovir, ethyldeoxyuridine, bromovinyldeoxyuridine, 5-iodo-5'-amino-2',5'-dideoxyuridine; steroid antiinflammatories, for example dexamethasone, hydrocortisone, prednisolone, fluorometholone, medrisone and possibly their esters, for example phosphoric acid esters; nonsteroid antiinflammatory agents, for example indomethacin, oxyphenbutazone, flurbiprofen; wound healers such as the epidermal growth factor EGF; local anesthetics, such as Benoxinate, proparacain and possibly their salts; cholinergic agonist drugs such as pilocarpine, methacholine, carbamylcholine, aceclidine, physostigmine, neostigmine, demecarium and possibly their salts; cholinergic antagonist drugs such as atropine and its salts; adrenergic agonist drugs such as noradrenalin, adrenalin, naphazoline, methoxamine and possibly their salts; adrenergic blockers such as propanolol, timolol, pindolol, bupranolol, atenolol, metoprolol, oxprenolol, practolol, butoxamine, sotalol, butedrin, labetalol and possibly their salts.

Also, associations of such drugs between themselves and possibly with other principles may be used as component 1) according to the invention. If, in the place of one single active substance 1), associations of active substances are used, such as those named above, the salts between the basic active substances and the partial carboxymethylpolysaccharide ester may be mixed salts of one or more of such basic substances or possibly mixed salts of this type with a certain number of further acid groups of the polysaccharide salified with the aforesaid bases or metals. For example it is possible to prepare salts of a partial ester of carboxymethylpolysaccharide acid with a pharmacologically inactive alcohol, for example an inferior alkanol and with a certain percentage of acid groups salified with the antibiotic kanamycin, another percentage salified with the vasoconstrictor phenylephrine, there then being possibly a remaining percentage of acid groups free or salified for example with sodium or one of the other abovesaid metals.

Examples of active substances to be used alone or in associations between themselves or with other active principles in dermatology are: therapeutic agents such as anti-infectious agents, antibiotics, antimicrobials, antiinflammatories, cytostatics, cytotoxics, antivirals, anesthetics, and preventive agents, such as sun shields, deodorants, antiseptics and disinfectants. Among the antibiotics are erythromycin, bacitracin, gentamycin, neomycin, aureomycin, gramicidin and associations of the same, the antibacterials and disinfectants include nitrofurazone, mafenide, clorexidine, and derivatives of 8-hydroxychinoleine and possibly their salts; the antiinflammatories include above all corticosteroids such as prednisolone, dexamethasone, flumethasone, clobetasol, acetonide of triamcinolone, betamethasone or their esters, as valerianates, benzoates, dipropionates; as cytotoxics fluorouracil, methotrexate, podophyllin; among the anesthetics are dibucaine, lidocaine, benzocaine.

The items in this list are of course only examples and any other agent described in literature may be used.

From the examples given for ophthalmology and dermatology it is possible to deduce which medicaments according to the present invention are to be used in the above fields of medicine, for example in otorhinolaryngology or odontology or in internal medicine, for example in endocrinology, where it is possible to use preparations for intradermal absorption or through the mucus, for example rectal or intranasal absorption, for example as nasal sprays or for inhalation into the oral cavity or into the pharynx.

Such preparations may therefore be for example antiinflammatories, or vasoconstrictors or vasopressors such as those named for ophthalmology, vitamines, antibiotics, such as those named above, hormones, chemotherapeutic agents, antibacterials, etc. also as named above for use in dermatology The medicaments according to the invention may be in solid form, for example as freeze-dried powders containing only the two components mixed together or prepared separately.

Such medicaments in solid form, on contact with the epithelium to be treated, more or less concentrated solutions according to the nature of the particular epithelium, with the same characteristics as the solutions previously prepared in vitro and which represent another particularly important aspect of the present invention. Such solutions are preferably in distilled water or in sterile physiological solutions and contain preferably no other pharmaceutical vehicle other than carboxymethylpolysaccharide ester or one of its salts. Concentrations of such solutions may also vary within a wide range, for example between 0.01 and 75% both for each of the two separate components and for their mixtures or salts. Particular preference is given to solutions with a marked elastic, viscous character, for example with a content of between 10% and 90% of the medicament or of each of its two components.

Particularly important are medicaments of this type, both in an anhydrous form (freeze-dried powders) or as solutions, either concentrated or diluted in water or saline, possibly with the addition of additive or auxiliary substances, such as in particular disinfectant substances or mineral salts acting as buffer or others, for ophthalmic use.

Among the medicaments of the invention the ones to be chosen in each case, are the ones with a degree of acidity suitable for the environment to which they are to be applied, that is, with a physiologically tolerable pH. Adjustment of the pH, for example in the abovesaid salts of the partial ester with a basic active substance, can be done by suitably regulating the quantity of polysaccharide, of its salts and of the basic substance itself. Thus, for example, if the acidity of a salt of the partial ester with a basic substance is too high, the excess of free acid groups is neutralized with the abovesaid inorganic bases, for example with sodium, potassium or ammonium hydrate.

The pharmaceutical preparations containing therapeutically active carboxymethylpolysaccharide esters, possibly in the form of the abovesaid medicaments resulting from the association of components 1) and 2), contain common excipients and may be used for oral, rectal, parenteral, subcutaneous, local or intradermal use. They are therefore in solid or semisolid form, for example pills, tablets, gelatinous capsules, capsules, suppositories, soft gelatin capsules. For parenteral and subcutaneous use it is possible to use forms intended for intramuscular or intradermal use, or suitable for infusions or intravenous injections and can therefore be presented as solutions of the active compounds or as freeze-dried powders of the active compounds to be mixed with one or more pharmaceutically acceptable excipients or diluents, suitable for the abovesaid uses and whose osmolarity is compatible with the physiological fluids. For local use, preparations in the form of sprays come into consideration, for example nasal sprays, creams or ointments for topical use or sticking plasters specially prepared for intradermal administration. The preparations of the invention may be used for administration to man or animals. They contain preferably between 0.01% and 10% of active component per solutions, sprays, ointments and creams and between 1% and 100% and preferably between 5% and 50% of active compound for the preparations in solid form. The dosage to be administered depends on specific indications, on the desired effect and on the chosen administration route. Daily doses of such preparations can be deduced by considering that used for the corresponding known preparations for corresponding cures of the therapeutically active alcohol whose action is to be exploited. Thus, for example, dosage of a carboxymethylchitin ester with cortisone can be derived from its content of this steroid and from its usual dosage in the known pharmaceutical preparations.

One particular form of pharmaceutical preparations is represented by the abovesaid medicaments constituted by the association of a carboxymethylpolysaccharide ester by an active substance, for example for topical use. These may also be in solid form, for example as freeze-dried powders containing only the two components 1) and 2) in a mixture or packed separately. Such medicaments in solid form, on contact with the epithelium to be treated, create more or less concentrated solutions according to the nature of the particular epithelium with the same characteristics as the solutions previously prepared in vitro and which represent another particularly important aspect of the present invention. Such solutions are preferably in distilled water or in sterile physiological solutions and contain preferably no other pharmaceutical vehicle other than the ester of carboxymethylpolysaccharide or one of its salts Concentrations of such solutions may also vary within a wide range, for example between 0.01 and 75% both for each of the two separate components and for their mixtures or salts. Particular preference is give to solutions with a marked elastic, viscous character, for example with a content of between 10% and 90% of the medicament or of each of its two components Particularly important are medicaments of this type, both in an anhydrous form (freeze-dried powders) or as concentrated solutions or diluted in water or saline, possibly with the addition of additive or auxiliary substances, such as in particular disinfectant substances or mineral salts acting as buffer or others, for ophthalmic use.

Among the medicaments of the invention, the ones to be chosen in each case, are the ones with a degree of acidity suitable for the environment to which they are to be applied, that is, with a physiologically tolerable pH. Adjustment of the pH, for example in the abovesaid salts of carboxymethylpolysaccharide esters with a basic active substance, can be done by suitably regulating the quantity of polysaccharide, of its salts and of the basic substance itself. Thus, for example, if the acidity of a salt of a carboxymethylpolysaccharide ester with a basic substance is too high, it is neutralized with the excess of free acid groups with the abovesaid inorganic bases, for example with sodium, potassium or ammonium hydrate.

In the cosmetic articles according to the invention, the esters of carboxymethylpolysaccharides and their salts are mixed with excipients commonly used in the art and are for example those already listed above for pharmaceutical preparations. Above all are used creams, ointments, lotions for topical use in which the carboxymethylpolysaccharide ester or one of its salts may constitute the cosmetic active principle possibly with the addition of other cosmetically active principles, such as for example steroids, for example pregnenolone, or one of the principles reported above. In such preparations the polysaccharide ester may be an ester with a cosmetically active alcohol, such as dexpantenol, or also an ester with a cosmetically inactive alcohol, such as inferior aliphatic alcohol, for example one of those named. The effect is due to the intrinsic cosmetic properties of the polysaccharide component. The cosmetic articles can however be based on various other active principles, for example disinfectant substances or sunshields or waterproofing agents or regenerating or antiwrinkle substances, or odoriferous substances, especially perfumes. In this case the polysaccharide ester may itself be the active ingredient and derive from alcohols which have such properties, for example from superior aliphatic alcohols or terpene alcohols in the case of perfumes or may function above all as a vehicle for substances with such properties as are associated with them. Particularly important are therefore cosmetic compositions similar to the medicaments described above in which the pharmaceutically active component 1) is substituted by a cosmetological factor, and the respective salts. Use of the abovesaid esters deriving from alcohols used in the perfume industry represents a big step forward in technique, since it allows for slow, constant and prolonged release of the odorous principles.

An important application of the present invention concerns sanitary and surgical articles, the methods for their manufacture and their use. The invention therefore embraces all articles similar to those already on the market but containing an ester of carboxymethyl-cellulose, starch or -chitin, for example inserts or ophthalmic lenses.

Absolutely new surgical and sanitary articles according to the present invention are represented by esters of carboxymethyl-polysaccharide acid regenerated as such by appropriate organic solutions, suitable to be made into sheet or thread form, obtaining films, sheets and threads for use in surgery, as auxiliaries and skin substitutes in severe cases of damage to this organ, such as for example following burns, or as suture threads in surgical operations. The invention includes in particular these uses and a procedure for the preparation of such articles consisting of (a) forming a solution of polysaccharide ester or of one of its salts in a suitable organic solvent, for example a ketone, an ester or an aprotic solvent such as an amide of a carboxy acid, especially a dialkylamide or of an aliphatic acid with between 1 and 5 carbon atoms and deriving from alkyl groups with between 1 and 6 carbon atoms, and especially from an organic sulfoxide, that is a dialkylsulfoxide with alkyl groups with a maximum of 6 diethylsulfoxide and also especially a fluorurate solvent with a low boiling point, such as especially hexafluoro-isopropanol, (b) working this solution sheet or thread form and (c) removing the organic solvent by contact with another organic or aqueous solvent which will mix with the first solvent and in which the polysaccharide ester is insoluble, especially an inferior aliphatic alcohol, for example ethyl alcohol (Wet spinning), or, should a solvent with a not too high boiling point be used to prepare the solution of the polysaccharide derivative, (d) removing this solvent in dry conditions with a current of gas, especially suitably heated nitrogen (Dry spinning). Dry-wet spinning can also be used to great effect The threads obtained with the esters of carboxymethyl-polysaccharide acids may be used to prepare lints for use in the medication of injuries and in surgery. These lints have the extraordinary advantage of being biodegradable in the organism, thanks to the enzymes they contain. Such enzymes split the ester into carboxymethyl-polysaccharide acid and the corresponding alcohol, should an ester deriving from a therapeutically acceptable alcohol be used, such as ethyl alcohol.

Preparation of the abovesaid sanitary and surgical articles can include the addition of plastifying materials to improve their mechanical characteristics, such as in the case of threads, to improve their resistance to tangles. These plastifying materials may be for example alkaline salts of fatty acids, for example stearate of sodium or palmitate of sodium, the esters of organic acids with a high number of carbon atoms, etc. Another application of the new esters where their biodegradability is taken advantage of by the esterases present in the organism, is represented by the preparation of capsules for subcutaneous implantation of medicaments or microcapsules to be administered by injection, for example by subcutaneous or intramuscular route.

Of great importance is also the preparation of microcapsules containing the new esters, a problem-free method for their use, which up till now has been very limited, for the reasons explained above, and which opens up a whole new area of application where a retard effect is to be achieved by injection.

Another application in the medical and surgical sectors of the new esters lies in the preparation of a wide variety of solid inserts such as plates, discs, sheets, etc replacing the metal or synthetic plastic ones currently in use, in cases calling for temporary inserts to be removed after a certain length of time. Preparations containing animal collagen, being of a proteic nature, often give rise to unpleasant side effects, such as inflammation or rejection. In the case of the esters of the present invention, this danger is overcome.

Another application in the fields of medicine and surgery of the new esters according to the present invention is represented by preparations in expandable material, especially in the form of sponges, for the medication of injuries or various types of lesion.

The esterified carboxymethyl-polysaccharides of the present invention are extremely suitable, thanks to their viscosity in aqueous solutions, for the preparation of gels which can be widely used in the food industry, for example for the manufacture of ice creams, puddings and many other types of sweet dishes. They can also be used, thanks to their water retaining properties, for the conservation of frozen foods. Another property of the esters of carboxymethylderivatives of the above polysaccharides is their ability for form and to stabilize emulsions and they can therefore also serve in the food industry for the preparation of seasonings and for the stabilization of many drinks such as beer or fruit juices, sauces and syrups.

The ease with which the esters of the present invention form films and threads can be put to good use in the paper industry, for the manufacture of stickers or adhesive labels, in printing and in textile dyeing As emulsifiers they can be used for the manufacture of polishes, anti-foam agents, lactics and as stabilizers in the ceramics and detergent industries.

Use of the new esters according to the present invention (or also of previously known esters of this type) in the food industry presents various advantages over the polysaccharides usually used in the industry, for example alginic acid which has a tendency to precipitate in acid conditions. In the presence of calcium ions too the insoluble products constituted by calcium alginate may become separated, and for this reason the use of alkaline alginates is compromised whenever they are intended for use in liquids containing the abovesaid ions, for example in products containing milk or its derivatives. For this reason alkaline alginates were substituted by glycol esters of alginic acid, particularly propyleneglycol ester. Glycol esters may however be toxic to a certain degree and their use must therefore be kept within certain limits. These drawbacks do not exist for example in the case of the esters of monovalent alcohols of the present invention, which can be used preferably for the preparation of the abovesaid food additives.

Also regarding the other abovesaid uses, the new polysaccharide esters open up a choice of surrogates which are an improvement on the products already in use. From the following list of alcohols, which can be used as esterifying components for carboxymethyl-polysaccharides which are the basis of the present invention, those suitable for the use in question should be chosen. Thus for example for all uses 1)-9) in the abovesaid sectors of industry alcohols of the aliphatic series with a low or medium number of carbon atoms should be preferred, or also simple heterocyclic alcohols or araliphatic alcohols. The cycloaliphatic alcohols, in particular terpene alcohols should be used preferably for cosmetic products. As for the alcohols for use in the medicaments or pharmaceutical preparations described above, they are those to be considered as therapeutically active esterifying components, for example steroid or vitamin alcohols.

Alcohols of the aliphatic series to be used as esterifying components of the carboxy groups of carboxymethyl derivatives according to the various aspects of the present invention are for example those with a maximal of 34 carbon atoms, which may be saturated or unsaturated and which may possibly also be substituted by other free functional or functionally modified groups, such as amino, hydroxy, aldehydo, keto, mercapto, carboxy groups or by groups derived from these, such as hydrocarbyl or dihydrocarbylamino groups (hereafter the term "hydrocarbyl" should be taken to mean not only monovalent radicals of hydrocarbons for example of the $C_nH_2n+1$ type, but also bivalent or trivalent "alkylidenes"=$C_nH_{2n}$), ether or ester groups, acetal or ketal groups, thioether or thioester groups, and esterified carboxy groups or carbamidic groups perhaps substituted by one or two hydrocarbyl groups, by nitrile groups or by halogens.

In the abovesaid groups containing hydrocarbyl radicals these are preferably inferior aliphatic radicals, for example alkyls, with a maximum of 6 carbon atoms. Such alcohols may also be interrupted in the carbon atom chain by heteroatoms, such as oxygen, nitrogen and sulfur atoms.

It is preferable to choose alcohols substituted with one or two of the abovesaid functional groups Alcohols of the abovesaid group to be used preferably within the scope of the present invention are those with a maximum of 12 and especially 6 carbon atoms and in which the hydrocarbyl radicals in the abovesaid amino, ether, ester, thioether, thioester, aceto, ketal groups represent alkyl groups with a maximum of 4 carbon atoms, and also in the esterified carboxy or substituted carbamidic groups the hydrocarbyl groups are alkyls with the same number of carbon atoms, and in which the amino or carbamidic groups may be alkylene amino or alkylene carbamidic groups with a maximum of 8 carbon atoms. Of these alcohols, special mention should be made of those which are saturated and unsubstituted such as for example methyl, ethyl, propyl, isopropyl alcohols, n-butyl, isobutyl, tertbutyl alcohols, amyl alcohols, pentyl, hexyl, octyl, nonyl and dodecyl alcohols and above all those with a linear chain, such as n-octyl alcohol or n-dodecyl alcohol. Among the substituted alcohols of this group are bivalent alcohols such as ethylene glycol, popylene glycol or butylene glycol, trivalent alcohols such as glycerin, aldehydo-alcohols such as tartronic alcohol, carboxy alcohols such as lactic acid, for example α-oxypropionic acid, glycolic acid, malic acid, tartaric acids, citric acid, aminoalcohols, such as aminoethanol, aminopropanol, n-aminobutanol and their dimethylated and diethylated derivatives in the amino function, choline, pyrrolidinylethanol, piperidinylethanol, piperazinylethanol and the corresponding derivatives of n-propyl n-butyl alcohols, monothioethylenglycol and its alkyl derivatives, for example the ethylate derivative in the mercapto function.

Among the saturated superior aliphatic alcohols are for example cetyl alcohol and myricyl alcohol, but especially important for the aims of the present invention are unsaturated superior alcohols with one or two double bonds, such as especially those contained in many essential oils and having affinity with terpenes, for example citronellol, geraniol, nerol, nerolidol, linalool, farnesol, phytol. Of the inferior unsaturated alcohols, allyl alcohol and propargyl alcohol should be considered. Of the araliphatic alcohols, special mention should be made of those with one single benzene residue and in which the aliphatic chain has a maximum of 4 carbon atoms and in which the benzene residue may be substituted by between 1 and 3 methyl or hydroxy groups or by halogen atoms, especially by chlorine, bromine, iodine, and in which the aliphatic chain may be substituted by one or more functions chosen from the group constituted by free or mono or dimethylated amino groups or by pyrrolidine or piperidine groups. Of such alcohols special mention should be made of benzyl alcohol and phenethyl alcohol.

Alcohols of the cycloaliphatic or aliphatic cycloaliphatic series may derive from mono or polycyclic hydrocarbons and may have a maximum of 34 carbon atoms. Among the alcohols derived from single-ringed cyclic hydrocarbons, special mention should be made of those with a maximum of 12 carbon atoms, the rings having preferably between 5 and 7 carbon atoms, which may be substituted for example by between one and three inferior alkyl groups, such as methyl, ethyl, propyl or isopropyl groups. As specific alcohols of this group we can mention cyclohexanol, cyclohexanediol, 1,2,3-cyclohexanetriol and 1,3,5-cyclohexanetriol (phloroglucitol), inositol, and then the alcohols which derive from p-menthane, such as carvomenthol, menthol, and α and γ-terpineol, 1-terpineol, 4-terpineol and piperitol, or the mixture of these alcohols known as "terpineol", 1,4-and 1,8-terpin Of the alcohols deriving from hydrocarbons with condensed rings, for example those of the group including thujane, pinane or camphane, we can mention thujanol, sabinol, pinol hydrate, D and L-borneol and D and L-isoborneol.

Polycyclic cycloaliphatic aliphatic alcohols to be used for the esters of the present invention are sterols, cholic acids and steroids, such as sexual hormones and their synthetic analogues and particularly corticosteroids and their derivatives Thus for example the following can be used: cholesterol, dihydrocholesterol, epidihydrocholesterol, corpostanol, epicoprostanol, sitosterol, stigmasterol, ergosterol, cholic acid, deoxycholic acid, lithocholic acid, estriol, estradiol, equilenin, equilin and their alkyl derivatives, as well as their ethynyl and propynyl derivatives in position 17, for example 17 α-ethynyl-estradiol or 7-α-methyl-17-α-ethynylestradiol, pregnenolone, pregnandiol, testosterone and its derivatives, such as 17-α-methyltestosterone, 1,2-dehydrotestosterone and 17-α-methyl-1,2-dehydrotestosterone, alkynyl derivatives in position 17 of testosterone and 1,2-dehydrotestosterone, such as 17-α-ethynyltestosterone, 17-α-propynyltestosterone, norgestrel, hydroxyprogesterone, corticosterone, deoxycorticosterone, 19-nortestosterone, 19-nor-17-α-methyltestosterone and 19-nor-17-α-ethynyltestosterone, cortisone, hydrocortisone, prednisone, prednisolone, fludrocortisone, dexamethasone, betamethasone, paramethasone, flumethasone, fluocinolone, fluprednylidene, clobetasol, beclomethasone, aldosterone, deoxycorticosterone, alfaxalone, alfadolone, bolasterone and antihormones such as cyproterone.

Useful esterifying components for the esters of the present invention are genins (aglycons) of cardioactive glycosides, such as digitoxigenin, gitoxygenin, digoxygenin, strophanthidin, tigogenin and saponins.

Other alcohols for use according to the invention are vitamin alcohols, such as axerophthol, vitamins $D_2$ and $D_3$, aneurine, lactoflavine, ascorbic acid, riboflavine, thiamine, pantothenic acid Heterocyclic alcohols to be used are for example are furfuryl alcohol, alkaloids and derivatives such as atropine, scopolamine, cinchonine, cinchonidine, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homophenazine, acetophenazine, fluphenazine, N-hydroxyethylpromethazine chloride; thioxanthene drugs such as flupenthixol and clopenthixol; anticonvulsivants such as meprophendiol, antipsychotics such as opipramol; antiemetics such as oxypendyl; analgesics such as carbetidine and phenoperidine and methadol; hypnotics such as etodroxizine; anorexics such as benzhydrol and diphemethoxidine; minor tranquilizers such as hydroxyzine; muscle relaxants such as cinnamedrine, diphylline, mephenesin, methocarbamol, chlorphenesin, 2,2-diethyl-1,3-propanediol, guaifenesin, idrocilamide; coronary vasodialtors such as dipyridamole and oxyfedrine; adrenergic blockers such as propanolol, timolol, pindolol, bupranolol, atenolol, metoprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilatators such as isonicotiny alcohol; carbonic anhydrase inhibitors such as sulocarbilate; antiasthmatics and antiinflammatories such as tiaramide; sulfamidics such as 2-p-sulfanylanilinoethanol.

According to the procedure of the present invention carboxymethyl-polysaccharide esters may be prepared to advantage by starting with quaternary ammonium salts of carboxymethyl-polysaccharide acid with an etherifying agent in an organic solvent, preferably aprotic, such as inferior alkyl dialkylsulfoxides, especially dimethylsulfoxide, and inferior alkyl dialkylamides of aliphatic acids, such as dimethyl or diethyl formamide or dimethyl or diethyl acetamide.

Other solvents too should be considered however, which are not always aprotic, such as alcohols, ethers, ketones, esters, especially aliphatic or heterocyclic alcohols and ketones with low boiling points, such as hexafluoroisopropanol, trifluoroethanol. Reaction is carried out preferably within a temperature range of approximately 0° to 100°, and especially between approximately 25° and 75°, for example at about 30°. Esterification is effected preferably by gradually adding the esterifying agent to the abovesaid ammonium salt dissolved in one of the abovesaid solvents, for example in dimethylsulfoxide. The alkylating agents can be those mentioned above, especially hydrocarbyl halogens, for example alkyl halogens. As starting quaternary ammonium salts it is preferable to use inferior tetraalkylammonium salts, with the alkyl groups having preferably between 1 and 6 carbon atoms. Mainly, the tetrabutylammonium salt of carboxymethylpolysaccharide is used. These quaternary ammonium salts can be prepared by reacting a metal salt of acidic polysaccharide, preferably one of those mentioned above, especially sodium or potassium salt, in aqueous solution with a salified sulfonic resin with the quaternary ammonium base. Tetraalkylammonium salt of acidic polysaccharide can be obtained by freeze-drying the eluate.

The starting ammonium salts are soluble in the abovesaid aprotic solvents, so esterification of acidic polysaccharide is very easy and gives abundant yields. By this procedure alone therefore it is possible to exactly dose the number of carboxy groups of acidic polysaccharide to be esterified. One variation of the previously described procedure consists in reacting potassium salt or sodium salt of acidic polysaccharide, suspended in suitable solvent, such as dimethylsulfoxide, with a suitable alkylating agent in the presence of catalyzing quantities of a quaternary ammonium salt, such as tetrabutylammonium iodide.

The procedure makes it possible to obtain, as we have already said, the total esters of acidic polysaccharide, and also of substituted alcohols, such as glycols, which have till now been inaccessible.

The preparation of salts according to the invention can be effected in the known way, by bringing together solutions or suspensions, in water or in organic solvents, of the two components 1) and 2) and possibly of bases or basic salts of the above-said alkaline or alkaline earth metals or magnesium or aluminium in calculated quantities and isolating the salts in anhydrous amorphous form according to the known techniques. It is possible for example to first prepare aqueous solutions of the two components 1) and 2), freeing such components of aqueous solutions of their salts with suitable ion exchangers, bringing together the two solutions at a low temperature, for example between 0° and 20°, should the salt thus obtained be easily soluble in water it is freeze-dried, while salts note easily solubilized can be separated by centrifugation or filtration or decantation and possibly subsequently dried.

For these associated medicaments too the dose is based on that of the active principles used singly and can therefore be easily determined by an expert on the basis of the doses recommended for the corresponding known drugs.

Of the new products of the present invention particular emphasis should be placed on the esters described above and their salts and those featuring in the following illustrative examples.

The present invention also includes modifications in the preparation procedure, new esters and their salts, in which a procedure is interrupted at any one stage or in which it is begun with an intermediate compound and the remaining stages are carried out, or in which the starting products are formed in situ.

The invention is illustrated by the following examples, without however being limited in any way by the same.

EXAMPLE 1

Preparation of the Tetrabutylammonium Salt of Carboxymethylchitin 10 mEq. of sodium salt of a carboxylmethylchitin with a substitution rate of 0.99, prepared according to Trujillo (Carbohydrate Res. 7, 483 (1968), corresponding to 2.85 g of dry compound, are solubilized in 300 ml of distilled water. The solution is then passed through a thermostatic column regulated at 4° C. and containing 15 ml of sulfonic resin (Dowex 50×8) in the form of tetrabutylammonium.

The sodium-free eluate is freeze-dried.

Yield: 5.05 g.

EXAMPLE 2

Preparation of the Ethyl Ester of a Carboxymethylchitin with a Substitution Rate of 0.99

5.05 g (10 mEq) of tetrabutylammonium salt of a carboxymethylchitin with a substitution rate of 0.99 are solubilized in 200 ml of DMSO at 25° C. under agitation and in absolutely dry conditions.

1.56 g (10 mEq) of ethyl iodide are added and the solution is agitated overnight at 30° C.

1000 ml of ethyl acetate are slowly added drop by drop, the precipitate is separated by filtration and washed 3 times with 100 ml of ethyl acetate, then dried in high vacuum.

Yield: 2.90 g.

Quantitative determination of the ester groups is carried out according to the saponification method described on pages 169–172 of "Quantitative Organic Analysis Via Functional Groups" 4th Edition, John Wiley and Sons Publication and shows an ester group content of 3.41 mEq/g (theoretical 3.43).

EXAMPLE 3

Preparation of the Isopropyl Ester of a Carboxymethylchitin with a Substitution Rate of 0.99

5.05 g (10 mEq) of tetrabutylammonium salt of a carboxymethylchitin with a substitution rate of 0.99 are solubilized in 200 ml of DMSO at 25° C. under agitation and in absolutely dry conditions.

1.70 g (10 mEq) of 2-iodopropane are added and the solution is agitated overnight at 30° C.

1000 ml of ethyl acetate are slowly added drop by drop, the precipitate is separated by filtration and washed 3 times with 100 ml of ethyl acetate, then dried in high vacuum.

Yield: 3.0 g.

Quantitative determination of the ester groups is carried out according to the saponification method described on pages 169–172 of "Quantitative Organic Analysis Via Functional Groups" 4th Edition, John Wiley and Sons Publication and shows an ester group content of 3.23 mEq/g (theoretical 3.28).

EXAMPLE 4

Preparation of the Benzyl Ester of a Carboxymethylchitin with a Substitution Rate of 0.99

5.05 g (10 mEq) of tetrabutylammonium salt of a carboxymethylchitin with a substitution rate of 0.99 are solubilized in 200 ml of DMSO at 25° C. under agitation and in absolutely dry conditions.

1.71 g (10 mEq) of benzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.5 g.

Quantitative determination of the ester groups is carried out according to the saponification method described on pages 169–172 of "Quantitative Organic Analysis Via Functional Groups" 4th Edition, John Wiley and Sons Publication and shows an ester group content of 2.81 mEq/g (theoretical 2.83).

EXAMPLE 5

Preparation of the p-Bromo Benzyl Ester of a Carboxymethylchitin with a Substitution Rate of 0.99

5.05 g (10 mEq) of tetrabutylammonium salt of a carboxymethylchitin with a substitution rate of 0.99 are solubilized in 200 ml of DMSO at 25° C. under agitation and in absolutely dry conditions. 2.5 g (10 mEq) of p-bromobenzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.29 g.

Quantitative determination of the ester groups is carried out according to the saponification method described on pages 169–172 of "Quantitative Organic Analysis Via Functional Groups" 4th Edition, John Wiley and Sons Publication and shows an ester group content of 2.29 mEq/g (theoretical 2.31).

EXAMPLE 6

Preparation of the Myristyl Ester of a Carboxymethylchitin with a Substitution Rate of 0.99

5.05 g (10 mEq) of tetrabutylammonium salt of a carboxymethylchitin with a substitution rate of 0.99 are solubilized in 200 ml of DMSO at 25° C. under agitation and in absolutely dry conditions.

2.77 g (10 mEq) of myristylbromide are added and the solution is agitated overnight at 30° C. 1000 ml of ethyl acetate are slowly added drop by drop, the precipitate is separated by filtration and washed 3 times with 100 ml of ethyl acetate, then dried in high vacuum Yield: 4.57 g.

Quantitative determination of the ester groups is carried out according to the saponification method described on pages 169–172 of "Quantitative Organic Analysis Via Functional Groups" 4th Edition, John Wiley and Sons Publication and shows an ester group content of 2.16 mEq/g (theoretical 2.18).

EXAMPLE 7

Preparation of the Tetrabutylammonium Salt of a Carboxymethylcellulose with a Substitution Rate of 0.75 and Low Viscosity 10 mEq of sodium salt of a carboxymethylcellulose with a substitution rate of 0.75 and low viscosity (30 mPa.s, solution at 2% in distilled water at 20° C. by Hoppler viscosimeter), corresponding to 2,96 g of dry compound, are solubilized in 300 ml of distilled water. The solution is then passed through a thermostatic column regulated at 4° C. and containing 15 ml of sulfonic resin (Dowex $50 \times 8$) in the form of tetrabutylammonium.

The sodium-free eluate is freeze-dried.

Yield: 5.05 g.

EXAMPLE 8

Preparation of the Ethyl Ester of a Carboxymethylcellulose with a Substitution Rate of 0.75 and Low Viscosity 5.15 g (10 mEq) of tetrabutylammonium salt of a carboxymethylcellulose with a substitution rate of 0.75 and low viscosity, prepared as in example 7, are solubilized in 200 ml of DMSO at 25° C. under agitation and in absolutely dry conditions. 1.56 g (10 mEq) of ethyl iodide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 2.91 g.

Quantitative determination of the ester groups is carried out according to the saponification method described on pages 169–172 of "Quantitative Organic Analysis Via Functional Groups" 4th Edition, John Wiley and Sons Publication and shows an ester group content of 3.30 mEq/g (theoretical 3.31).

EXAMPLE 9

Preparation of the Isopropyl Ester of a Carboxymethylcellulose with a Substitution Rate of 0.75 and Low Viscosity 5.15 g (10 mEq) of tetrabutylammonium salt of a carboxymethylcellulose with a substitution rate of 0.75 and low viscosity, prepared as in example 7, are solubilized in 200 ml of DMSO at 25° C. under agitation and in absolutely dry conditions.

1.70 g (10 mEq) of 2-iodopropane are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.02 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.12 mEq/g (theoretical 3.16).

EXAMPLE 10

Preparation of the Isopropyl Ester of a Carboxymethylcellulose with a Substitution Rate of 0.75 and Low Viscosity 5.15 g (10 mEq) of tetrabutylammonium salt of a carboxymethylcellulose with a substitution rate of 0.75 and low viscosity, prepared as in example 7, are solubilized in 200 ml of DMSO at 25° C. under agitation and in absolutely dry conditions.

1.71 g (10 mEq) of benzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.54 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.70 mEq/g (theoretical 2.74).

EXAMPLE 11

Preparation of the p-Bromobenzyl Ester of a Carboxymethylcellulose with a Substitution Rate of 0.75 and Low Viscosity 5.15 g (10 mEq) of tetrabutylammonium salt of a carboxymethylcellulose with a substitution rate of 0.75 and low viscosity, prepared as in example 7, are solubilized in 200 ml of DMSO at 25° C. under agitation and in absolutely dry conditions.

2.5 g (10 mEq) of p-bromobenzyl-bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.35 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.25 mEq/g (theoretical 2.28).

EXAMPLE 12

Preparation of the Myristyl Ester of a Carboxymethylcellulose with a Substitution Rate of 0.75 and Low Viscosity 5.15 g (10 mEq) of tetrabutylammonium salt of a carboxymethylcellulose with a substitution rate of 0.75 and low viscosity, prepared as in example 7, are solubilized in 200 ml of DMSO at 25° C. under agitation and in absolutely dry conditions.

2.77 g (10 mEq) of myristyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.61 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.12 mEq/g (theoretical 2.15).

EXAMPLE 13

Preparation of the Tetrabutylammonium Salt of a Carboxymethylcellulose with a Substitution Rate of 0.75 and Medium Viscosity 10 mEq of sodium salt of a carboxymethylcellulose with a substitution rate of 0.75 and medium viscosity (30 mPa.s, solution at 2% in distilled water at 20° C. by Hoppler viscosimeter), corresponding to 2,96 g of dry compound, are solubilized in 300 ml of distilled water. The solution is then passed through a thermostatic column regulated at 4° C. and containing 15 ml of sulfonic resin (Dowex 50×8) in the form of tetrabutylammonium.

The sodium-free eluate is freeze-dried.

Yield: 5.00 g.

EXAMPLE 14

Preparation of the Ethyl Ester of a Carboxymethylcellulose with a Substitution Rate of 0.75 and Medium Viscosity 5.15 g (10 mEq) of tetrabutylammonium salt of a carboxymethylcellulose with a substitution rate of 0.75 and medium viscosity, prepared as in example 13, are solubilized in 200 ml of DMSO at 25° C. under agitation and in absolutely dry conditions.

1.56 g (10 mEq) of ethyl iodide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 2.93 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.24 mEq/g (theoretical 3.31).

EXAMPLE 15

Preparation of the Isopropyl Ester of a Carboxymethylcellulose with a Substitution Rate of 0.75 and Medium Viscosity 5.15 g (10 mEq) of tetrabutylammonium salt of a carboxymethylcellulose with a substitution rate of 0.75 and medium viscosity, prepared as in example 13, are solubilized in 200 ml of DMSO at 25° C. under agitation and in absolutely dry conditions.

1.7 g (10 mEq) of 2-iodopropane are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.1 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.11 mEq/g (theoretical 3.16).

EXAMPLE 16

Preparation of the Benzyl Ester of a Carboxymethylcellulose with a Substitution Rate of 0.75 and Medium Viscosity 5.15 g (10 mEq) of tetrabutylammonium salt of a carboxymethylcellulose with a substitution rate of 0.75 and medium viscosity, prepared as in example 13, are solubilized in 200 ml of DMSO at 25° C. under agitation and in absolutely dry conditions. 1.71 g (10 mEq) of benzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.04 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.70 mEq/g (theoretical 2.74).

EXAMPLE 17

Preparation of the p-Bromo Benzyl Ester of a Carboxymethylcellulose with a Substitution Rate of 0.75 and Medium Viscosity 5.15 g (10 mEq) of tetrabutylammonium salt of a carboxymethylcellulose with a substitution rate of 0.75 and medium viscosity, prepared as in example 13, are solubilized in 200 ml of DMSO at 25° C. under agitation and in absolutely dry conditions.

2.5 g (10 mEq) di p-bromobenzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.32 g.

Quantitative determination of the ester groups is carried out according to the saponification method described on pages 169-172 of "Quantitative Organic Analysis Via Functional Groups" 4th Edition, John Wiley and Sons Publication and shows an ester group

EXAMPLE 18

Preparation of the Myristyl Ester of a Carboxymethylcellulose with a Substitution Rate of 0.75 and Medium Viscosity 5.15 g (10 mEq) of tetrabutylammonium salt of a carboxymethylcellulose with a substitution rate of 0.75 and medium viscosity, prepared as in example 13, are solubilized in 200 ml of DMSO at 25° C. under agitation and in absolutely dry conditions.

2.77 g (10 mEq) of myristyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.61 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.12 mEq/g (theoretical 2.15).

EXAMPLE 19

Preparation of the Tetrabutylammonium Salt of a Carboxymethylcellulose with a Substitution Rate of 0.75 and High Viscosity 10 mEq of sodium salt of a carboxymethylcellulose with a substitution rate of 0.75 and high viscosity (6000 mPa.s, solution at 2% in distilled water at 20° C. by Hoppler viscosimeter), corresponding to 2.96 g of dry compound, are solubilized in 300 ml of distilled water The solution is then passed through a thermostatic column regulated at 4° C. and containing 15 ml of sulfonic resin (Dowex 50×8) in the form of tetrabutylammonium.

The sodium-free eluate is freeze-dried.

Yield: 4.95 g.

EXAMPLE 20

Preparation of the Ethyl Ester of a Carboxymethylcellulose with a Substitution Rate of 0.75 and High Viscosity 5.15 g (10 mEq) of tetrabutylammonium salt of a carboxymethylcellulose with a substitution rate of 0.75 and high viscosity, prepared as in example 19, are solubilized in 200 ml of DMSO at 25° C. under agitation and in absolutely dry conditions.

1.56 g (10 mEq) of ethyl iodide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 2.91 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.30 mEq/g (theoretical 3.31).

EXAMPLE 21

Preparation of the Isopropyl Ester of a Carboxymethylcellulose with a Substitution Rate of 0.75 and High Viscosity 5.15 g (10 mEq) of tetrabutylammonium salt of a carboxymethylcellulose with a substitution rate of 0.75 and high viscosity, prepared as in example 19, are solubilized in 200 ml of DMSO at 25° C. under agitation and in absolutely dry conditions.

1.7 g (10 mEq) of 2-iodopropane are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.02 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.07 mEq/g (theoretical 3.16).

EXAMPLE 22

Preparation of the Benzyl Ester of a Carboxymethylcellulose with a Substitution Rate of 0.75 and High Viscosity 5.15 g (10 mEq) of tetrabutylammonium salt of a carboxymethylcellulose with a substitution rate of 0.75 and high viscosity, prepared as in example 19, are solubilized in 200 ml of DMSO at 25° C. under agitation and in absolutely dry conditions.

1.71 g (10 mEq) of benzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.46 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.72 mEq/g (theoretical 2.74).

EXAMPLE 23

Preparation of the p-Bromo Benzyl Ester of a Carboxymethylcellulose with a Substitution Rate of 0.75 and High Viscosity 5.15 g (10 mEq) of tetrabutylammonium salt of a carboxymethylcellulose with a substitution rate of 0.75 and high viscosity, prepared as in example 19, are solubilized in 200 ml of DMSO at 25° C. under agitation and in absolutely dry conditions.

2.5 g (10 mEq) of p-bromobenzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.28 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.26 mEq/g (theoretical 2.28).

EXAMPLE 24

Preparation of the Myristyl Ester of a Carboxymethylcellulose with a Substitution Rate of 0.75 and High Viscosity 5.15 g (10 mEq) of tetrabutylammonium salt of a carboxymethylcellulose with a substitution rate of 0.75 and high viscosity, prepared as in example 19, are solubilized in 200 ml of DMSO at 25° C. under agitation and in absolutely dry conditions.

2.77 g (10 mEq) of myristyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.54 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.11 mEq/g (theoretical 2.15).

EXAMPLE 25

Preparation of the Tetrabutylammonium Salt of a Carboxymethylcellulose with a Substitution Rate of 1.0 and Medium Viscosity 10 mEq of sodium salt of a carboxymethylcellulose with a substitution rate of 1.0 and medium viscosity (200 mPa.s, solution at 2% in distilled water at 20° C. by Hoppler viscosimeter), corresponding to 2,42 g of dry compound, are solubilized in 300 ml of distilled water. The solution is then passed through a thermostatic column regulated at 4° C. and containing 15 ml of sulfonic resin (Dowex 50×8) in the form of tetrabutylammonium.

The sodium-free eluate is freeze-dried.

Yield: 4.6 g.

EXAMPLE 26

Preparation of the Ethyl Ester of a Carboxymethylcellulose with a Substitution Rate of 1.0 and Medium Viscosity 4.62 g (10 mEq) of tetrabutylammonium salt of a carboxymethylcellulose with a substitution rate of 1.0 and medium viscosity, prepared as in example 25, are solubilized in 200 ml of DMSO at 25° C. under agitation and in absolutely dry conditions.

1.56 g (10 mEq) of ethyl iodide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield 2.44 g.

Quantitative determination of the ester groups is carried out according to the saponification method described on pages 169-172 of "Quantitative Organic Analysis Via Functional Groups" 4th Edition, John Wiley and Sons Publication and shows an ester group content of 4.0 mEq/g (theoretical 4.03)

EXAMPLE 27

Preparation of the Isopropyl Ester of a Carboxymethylcellulose with a Substitution Rate of 1 0 and Medium Viscosity 4.62 g (10 mEq) of tetrabutylammonium salt of a carboxymethylcellulose with a substitution rate of 1.0 and medium viscosity, prepared as in example 25, are solubilized in 200 ml of DMSO at 25° C. under agitation and in absolutely dry conditions.

1.70 g (10 mEq) of 2-iodopropane are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 2.58 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.69 mEq/g (theoretical 3.81).

EXAMPLE 28

Preparation of the Benzyl Ester of a Carboxymethylcellulose with a Substitution Rate of 1.0 and Medium Viscosity 4.62 g (10 mEq) of tetrabutylammonium salt of a carboxymethylcellulose with a substitution rate of 1.0 and medium viscosity, prepared as in example 25, are solubilized in 200 ml of DMSO at 25° C. under agitation and in absolutely dry conditions.

1.71 g (10 mEq) of benzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.05 g.

Quantitative determination of the ester groups is carried out according to the saponification method described on pages 169-172 of "Quantitative Organic Analysis Via Functional Groups" 4th Edition, John Wiley and Sons Publication and shows an ester group content of 3.15 mEq/g (theoretical 3.22)

EXAMPLE 29

Preparation of the p-Bromobenzyl Ester of a Carboxymethylcellulose with a Substitution Rate of 1.0 and Medium Viscosity 4.62 g (10 mEq) of tetrabutylammonium salt of a carboxymethylcellulose with a substitution rate of 1.0 and medium viscosity, prepared as in example 25, are solubilized in 200 ml of DMSO at 25° C. under agitation and in absolutely dry conditions.

2.5 g (10 mEq) of p-bromobenzyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 3.85 g.

Quantitative determination of the ester groups is carried out according to the saponification method described on pages 169-172 of "Quantitative Organic Analysis Via Functional Groups" 4th Edition, John Wiley and Sons Publication and shows an ester group

EXAMPLE 30

Preparation of the Myristyl Ester of a Carboxymethylcellulose with a Substitution Rate of 1.0 and Medium Viscosity 4.62 g (10 mEq) of tetrabutylammonium salt of a carboxymethylcellulose with a substitution rate of 1.0 and medium viscosity, prepared as in example 25, are solubilized in 200 ml of DMSO at 25° C. under agitation and in absolutely dry conditions.

2.77 g (10 mEq) of myristyl bromide are added and the solution is agitated overnight at 30° C.

1000 ml of ethyl acetate are slowly added drop by drop, the precipitate is separated by filtration and washed 3 times with 100 ml of ethyl acetate, then dried in high vacuum Yield: 4.12 g.

Quantitative determination of the ester groups is carried out according to the saponification method described on pages 169-172 of "Quantitative Organic Analysis Via Functional Groups" 4th Edition, John Wiley and Sons Publication and shows an ester group content of 2.36 mEq/g (theoretical 2.4).

As discussed above, the new polysaccharide esters of the invention are useful for the preparation of pharmaceutical formulations and new medical articles. The following are particular exemplary pharmaceutical preparations according to the invention.

Formulation 1

Collirium containing cortisone of which 100 ml contain:

Partial ester of carboxymethylcellulose with cortisone, gr. 0.200 ethyl p. hydroxybenzoate, gr. 0.010 methyl p. hydroxybenzoate, gr. 0.050 sodium chloride, gr. 0.900 water for injectable preparations/q.b.a., ml. 100

Formulation 2

Injectable solution containing hydrocortisone of which 100 ml contain:

partial ester of carboxymethylchitin with hydfocortisone, gr. 0.1 water for injectable preparations/q.b.a., ml. 100

Formulation 3

Cream containing a partial ester of carboxymethylcellulose with ethyl alcohol, of which 100 gr. contain:

partial ester of carboxymethylcellulose acid with ethyl alcohol, gr. 0.2

Polyethyleneglycol monostearate 400, gr. 10.000

Cetiol V. gr. 5.000

Lanette SX, gr. 2.000

Paraoxybenzoate of methyl, gr. 0.075

Paraoxybenzoate of propyl, gr. 0.050

Sodium dihydroacetate, gr. 0.100

Glycerine F.U., gr. 1.500

Sorbitol 70, gr. 1.500

Test cream, gr. 0.050

Water for injectable preparations/q.b.a., gr. 100.00

The following preparations exemplify the medical articles according to the invention containing the alginic esters.

EXAMPLE 31

Preparation of Films Using Esters of Carboxymethylcellulose

A solution is prepared in dimethylsulfoxide of the n-propyl ester of carboxymethylcellulose.

By means of a stratifier, a thin layer of solution is spread on a glass sheet; the thickness must be 10 times greater than the final thickness of the film. The glass sheet is immersed in ethanol which absorbs the dimethylsulfoxide but does not solubilize the carboxymethylcellulose ester which becomes solid. The film is detached from the glass sheet, is repeatedly washed with ethanol, then with water and then again with ethanol.

The resulting sheet is dried in a press for 48 hours at 30°.

EXAMPLE 32

Preparation of Threads Using Esters of Carboxymethylcellulose

A solution is prepared in dimethylsulfoxide of the benzyl ester of carboxymethylcellulose. The solution thus obtained is pressed by means of a pump through a threader with 0.5 mm holes.

The threader is immersed in ethanol/dimethylsulfoxide 80:20 (this concentration is kept constant by continuous addition of ethanol); when the solution in dimethylsulfoxide is soaked in this way it tends to lose most of the dimethylsulfoxide and the thread solidifies.

The thread is stretched while it still has a content of dimethylsulfoxide, is then repeatedly stretched and washed with ethanol The thread is dried in nitrogen current.

EXAMPLE 33

Preparation of a Spongy Material Made with Esters of Carboxymethylcellulose 1 g of benzyl ester of carboxymethylcellulose in which all the carboxylic groups are esterified (obtained for example as described in Example 22) are dissolved in 5 ml of dimethylsulfoxide. To each 10 ml of solution prepared, a mixture of 31.5 g of sodium chloride with a degree of granularity corresponding to 300µ, 1.28 g of sodium bicarbonate and 1 g of citric acid is added and the whole is homogenized in a mixer.

The pasty mixture is stratified in various ways, for instance by means of a mange consisting of two rollers which turn opposite each other at an adjustable distance between the two. Regulating this distance the paste is passed between the rollers together with a strip of silicone paper which acts as a support to the layer of paste thus formed. The layer is cut to the desired dimensions of length and breadth, removed from the silicone, wrapped in filter paper and emerged in a suitable solvent, such as water. The sponges thus obtained are washed with a suitable solvent such as water and possibly sterilized with gamma rays.

EXAMPLE 34

Preparation of a Spongy Material Made with Esters of Carboxymethylcellulose

In the manner described in Example 33, it is possible to prepare spongy materials with other carboxymethylcellulose esters. In the place of dimethylsulfoxide it is possible to use, if desired, any other solvent capable of dissolving the chosen ester. In the place of sodium chloride it is possible to use any other solid compound which is insoluble in the solvent used to dissolve the carboxymethylcellulose ester, but which is soluble in the solvent used to precipitate the carboxymethylcellulose ester after the above mentioned mechanical treatment, and finally which has the correct degree of granularity to obtain the type of pores desired in the sponge material.

In the place of sodium bicarbonate and citric acid it is possible to use other couples of similar compounds, that is, compounds which react to each other in suspension or solution of the solvent used to dissolve carboxymethylcellulose in such a way as to form a gas, such as carbon dioxide, which has the effect of producing a less compact spongy material. In this way it is possible to use, in the place of sodium bicarbonate, other bicarbonates or alkaline or alkaline earth carbonates and in the Place of citric acid other acids in solid form, such as tartaric acid.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. Total and partial esters of acidic polysaccharides chosen from the group consisting of carboxymethylcellulose, carboxymethyl starch and carboxymethylchitin with an alcohol selected from the group consisting of aliphatic, araliphatic, cycloaliphatic and heterocyclic alcohols and salts of such partial esters with inorganic or organic bases, with the exception of the partial esters of carboxymethylcellulose with ethylene or propyleneglycol and carboxymethyl starch with methyl or benzyl alcohols.

2. Esters of acidic polysaccharides and their salts according to claim 1, in which the aliphatic alcohols have a maximum of 34 carbon atoms and are unsubstituted or substituted by one or two functional groups chosen from the group consisting of amino, hydroxy, mercapto, aldehydo, keto, carboxy, hydrocarbyl and dihydrocarbylamino, ether, ester, thioether, thioester, acetal, ketal, carbalkoxy groups, carbamidic and substituted carbamidic groups by one or two alkyl groups with the hydrocarbyl radicals in these functionally modified groups having a maximum of 6 carbon atoms, and in which such alcohols of the aliphatic series may be interrupted in the carbon atom chain by heteroatoms chosen from the group formed by oxygen, sulfur and nitrogen.

3. Esters of acidic polysaccharides and their salts according to claim 2, wherein said aliphatic alcohol has a maximum of 12 carbon atoms; said hydrocarbyl radicals have a maximum of 4 carbon atoms; and wherein said amino or substituted carbamidic groups may also be alkyleneamino groups or alkylenecarbamidic groups with a maximum of 8 carbon atoms.

4. Esters of acidic polysaccharides and their salts according to claim 3, wherein said alcohol is ethyl, propyl, isopropyl, n-butyl, isobutyl, tert-butyl alcohols, an amyl, pentyl, hexyl or octyl alcohol.

5. Esters of acidic polysaccharides and their salts according to claim 3, wherein said alcohol is glycerin.

6. Esters of acidic polysaccharides and their salts according to claim 3, wherein said esterifying alcohol is tartronic alcohol, lactic acids, glycolic acid, malic acid, a tartaric acid or citric acid.

7. Esters of acidic polysaccharides and their salts according to claim 3, wherein the esterifying alcohol is aminoethanol, aminopropanol, n-aminobutanol or di-methyl or diethyl derivatives thereof in the amino function, choline, pyrrolidinylethanol, piperidinylethanol, piperazinylethanol or the corresponding derivatives of n-propyl or n-butyl alcohols, or monothioethyleneglycol or its lower alkylderivatives in the mercapto function.

8. Esters of acidic polysaccharides and their salts according to claim 3, wherein the esterifying alcohol component is a higher aliphatic alcohol chosen from the group formed by cetyl, myricyl alcohols, citronellol, geraniol, nerol, nerolidol, linalool, farnesol, and phytol 9. Esters of acidic polysaccharides and their salts according to claim 1, wherein the alcohols of the araliphatic alcohols are those with only one benzene residue and in which the aliphatic chain has a maximum of 4 carbon atoms and in which the benzene residue may be substituted by between 1 and 3 methyl or hydroxy groups, by halogen atoms, and in which the aliphatic chain may be substituted by one or two functions chosen from the group consisting of free amino or mono- or diethyl groups or by pyrrolidine or piperidine groups.

10. Esters of acid polysaccharides and their salts according to claim 9, wherein the alcohol is chosen from the group consisting of benzyl alcohol, phenethyl alcohol, ephedrine and adrenaline.

11. Esters of acidic polysaccharides and their salts according to claim 1, wherein the alcohols of the cycloaliphatic or aliphatic cycloaliphatic or heterocyclic series respectively derive from mono- or polycyclic hydrocarbons with a maximum or 34 carbon atoms and are unsubstituted or substituted by one or more functional groups chosen from the group formed by amino, hydroxy, mercapto, aldehydo, keto, carboxy, hydrocarbyl and dihydrocarbylamino, ether, ester, thioether, thioester, acetal, ketal, carbalkoxy, carbamidic and substituted carbamidic groups by one or two alkyl groups with the hydrocarbyl radicals in these functionally modified groups having a maximum of 6 carbon atoms, and which may be interrupted in the carbon atom chain by heteroatoms chosen from the group formed by —O—, —N—, —N—, —S—, and which may have one or more bonds, including aromatic structures.

12. Esters of acidic polysaccharides and their salts according to claim 11, in which the alcohols are monocyclic having a maximum of 12 carbon atoms and the ring having between 5 and 7 carbon atoms possibly substituted by between one and three lower alkyl groups.

13. Esters of acidic polysaccharides and their salts according to claim 11, in which the polycyclic alcohols are sterines, cholic acids, or steroid alcohols.

14. Esters of acidic polysaccharides and their salts according to claim 11, in which the alcohols are chosen from the group consisting of alkaloids, phenethylamines, phenothiazine drugs, thioxanthenes, anticonvulsivants, antipsychotics, antiemetics, analgesics, hypnotics, anorexics, tranquilizers, muscle relaxants, coronary vasodilators, adrenergic blockers, narcotic antagonists, antineoplastics, antibiotics, antivirals, peripheral vasodilators, carbonic anhydrase inhibitors, antiasthmatics, antiinflammatories and sulfamidics.

15. Esters of acidic polysaccharides according to any one of claims 1–14, in which all the carboxy groups are esterified with an alcohol.

16. Esters of acidic polysaccharides and their salts according to claim 1, in which at least 5% and at the most 95% of all the carboxy groups are esterified.

17. Salts of partial esters according to any one of claims 1–14, wherein said inorganic base is an alkaline metal, an alkaline earth metal, magnesium or aluminum 18. Sodium or ammonium salts according to claim 17.

19. Salts of partial esters according to claim 1, wherein said organic base is an aliphatic, araliphatic, cycloaliphatic or heterocyclic amino base.

20. Salts of partial esters according to claim 19, in which the amines are therapeutically acceptable bases.

21. Salts of partial esters according to claim 20 in which the amines are chosen from the group consisting of: alkaloids, peptides, phenothiazines, benzodiazepines, thioxantenes, hormones, vitamins, anticonvulsivants, antipsychotics, antiemetics, anesthetics, hypnotics, anorexics, tranquilizers, muscle relaxants, coronary vasodilators, antineoplastics, antibiotics, antibacterials, antivirals, antimalarials, carbonic anhydrase inhibitors, nonsteroid antiinflammatories, vasoconstrictors, cholinergic agonists, cholinergic blockers, adrenergic agonists, adrenergic blockers, and narcotic antagonists.

22. Salts of partial esters according to claim 20, in which the amines are pharmacologically inactive and are chosen from the group consisting of mono-, di- and tri-alkylamines with a maximum of 8 carbon atoms, arylalkylamines with a maximum of 8 carbon atoms in the aliphatic part and with a benzene group as the aromatic part, optionally substituted by between 1 and 3 methyl groups or halogen atoms or hydroxy groups, alkyleneamines with cycles of between 4 and 6 carbon atoms, optionally interrupted in the cycle of heteroatoms chosen from the group formed by 0 and S, and amines of all these types substituted by amino or hydroxy functions.

23. An ester of an acidic polysaccharide according to claim 1, wherein said ester is a compound chosen from the group consisting of an ethyl, isopropyl, benzyl, p-bromo-benzyl, and mirystyl ester of carboxymethylchitin.

24. An ester of an acidic polysaccharide according to claim 1, wherein said ester is a compound chosen from the group consisting of an ethyl, isopropyl, benzyl, p-bromo-benzyl, and mirystyl ester of carboxymethylcellulose.

25. A pharmaceutical preparation or medicament which comprises:
1) a therapeutically effective amount of a pharmacologically active substance or an association of pharmacologically active substances; and
2) a vehicle comprised of a total or partial ester of carboxymethylcellulose, of carboxymethylchitin or of carboxymethyl starch or a salt of such partial esters with an inorganic or organic base.

26. A pharmaceutical preparation or medicament which comprises a total or partial ester of carboxymethylcellulose, of carboxymethylchitin or of carboxymethyl starch with an alcohol and salts of such partial esters with inorganic or organic bases, in which at least one of said alcohols and said base is therapeutically active.

27. A pharmaceutical preparation or medicament according to any one of claims 25 and 26, in which the active substance is for topical use.

28. Total and partial esters of carboxymethylchitin with an alcohol selected from the group consisting of aliphatic, araliphatic, cycloaliphatic and heterocyclic alcohols.

29. Esters of carboxymethylchitin and their salts according to claim 28, wherein said alcohol is ethyl, propyl. isopropyl, n-butyl, isobutyl, tert-butyl alcohols, an amyl, pentyl, hexyl or octyl alcohol.

30. Esters of carobxymethylchitin and their salts according to claim 28, wherein said alcohol is glycerin.

31. Esters of carboxymethylchitin and their salts according to claim 28, wherein said esterifying alcohol is tartronic alcohol, lactic acids, glycolic acid, malic acid, a tartaric acid or citric acid.

32. Esters of carboxymethylchitin and their salts according to claim 28, wherein the esterifying alcohol is aminoethyl, aminopropanol, n-aminobutanol or di-methyl or diethyl derivatives thereof in the amino function, choline, pyrrolidinylethanol, piperidinylethanol, piperazinylethanol or the corresponding derivatives of n-propyl or n-butyl alcohols, or monothioethyleneglycol or its lower alkylderivatives in the mercapto function.

33. Esters of carboxymethylchitin and their salts according to claim 28, wherein the esterifying alcohol component is a higher aliphatic alcohol chosen from the group consisting of cetyl, myricyl alcohols, citronellol, geraniol, nerol, nerolidol, linalool, farnesol, and phytol.

34. Esters of carboxymethylchitin and their salts according to claim 28, wherein the alcohol is chosen from the group consisting of benzyl alcohol, phenethyl alcohol. ephedrine and adenaline.

35. Esters of carboxymethylchitin according to any one of claims 29-34, in which all the carboxy groups are esterified with an alcohol.

36. Salts of partial esters according to any one of claims 29-34, wherein said inorganic base is an alkaline metal, an alkaline earth metal, magnesium or aluminum.

37. Sodium or ammonium salts according to claim 28.

38. Salts of partial esters according to claim 28, wherein said organic base is an aliphatic, araliphatic, cycloaliphatic or heterocyclic amino base.

39. Salts of partial esters according to claim 28, in which the amines are therapeutically acceptable bases.

40. An ester of carboxymethylchitin according to claim 28, wherein said alcohol is ethyl alcohol.

41. An ester of carboxymethylchitin according to claim 28, wherein said alcohol is isopropyl alcohol.

42. An ester of carboxymethylchitin according to claim 28, wherein said alcohol is benzyl alcohol.

43. An ester of carboxymethylchitin according to claim 28, wherein said alcohol is p-bromobenzyl alcohol.

44. An ester of carboxymethylchitin according to claim 28, wherein said alcohol is myristyl alcohol.

45. A pharmaceutical preparation which comprises:
   1) between 0.01 and 75% of a pharacologically active substance or an association of pharmacologically active substances; and
   2) a vehicle comprised of a total or partial ester according to claim 1.

46. A pharmaceutical preparation which comprises:
   1) between 0.01 and 75% of a pharacologically active substance or an association of pharmacologically active substances; and
   2) a vehicle comprised of a total or partial ester according to claim 28.

47. A pharmaceutical preparation in the form of a solution, spray ointment or cream which comprises:
   1) between 0.01 and 10% of a pharacologically active substance or an association of pharmacologically active substances; and
   2) a vehicle comprised of a total or partial ester according to claim 1.

48. A pharmaceutical preparation in the form of a solution, spray ointment or cream which comprises:
   1) between 0.01 and 10% of a pharacologically active substance or an association of pharmacologically active substances; and
   2) a vehicle comprised of a total or partial ester according to claim 28.

49. A pharmaceutical preparation in a solid form which comprises:
   1) between 5 and 50% of a pharacologically active substance or an association of pharmacologically active substances; and
   2) a vehicle comprised of a total or partial ester according to claim 1.

50. A pharmaceutical preparation in a solid form which comprises:
   1) between 5 and 50% of a pharacologically active substance or an association of pharmacologically active substances; and
   2) a vehicle comprised of a total or partial ester according to claim 28.

* * * * *